United States Patent
Iwahashi et al.

(10) Patent No.: US 9,753,082 B2
(45) Date of Patent: Sep. 5, 2017

(54) INSPECTION METHOD FOR SEMICONDUCTOR SUBSTRATE, MANUFACTURING METHOD OF SEMICONDUCTOR DEVICE AND INSPECTION DEVICE FOR SEMICONDUCTOR SUBSTRATE

(71) Applicant: Toyota Jidosha Kabushiki Kaisha, Toyota-shi Aichi-ken (JP)

(72) Inventors: Yohei Iwahashi, Okazaki (JP); Hidemi Senda, Toyota (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 22 days.

(21) Appl. No.: 15/055,200

(22) Filed: Feb. 26, 2016

(65) Prior Publication Data

US 2016/0252571 A1    Sep. 1, 2016

(30) Foreign Application Priority Data

Feb. 27, 2015    (JP) ................................ 2015-038648

(51) Int. Cl.
*G01R 31/00* (2006.01)
*G01R 31/28* (2006.01)
(Continued)

(52) U.S. Cl.
CPC ......... *G01R 31/2875* (2013.01); *G01R 31/26* (2013.01); *H01L 22/14* (2013.01);
(Continued)

(58) Field of Classification Search
CPC ....... H01L 21/00; H01L 2221/00; G01R 1/00; G01N 1/00; G01N 2201/00
See application file for complete search history.

(56) References Cited

U.S. PATENT DOCUMENTS

| 5,977,783 A * | 11/1999 | Takayama ........ G01R 1/06761 324/755.01 |
| 2007/0063721 A1* | 3/2007 | Dozier ............... G01R 31/2889 324/750.14 |

(Continued)

FOREIGN PATENT DOCUMENTS

| JP | 2010-186851 A | 8/2010 |
| JP | 2013-096837 A | 5/2013 |
| JP | 2014-219273 A | 11/2014 |

*Primary Examiner* — Jermele M Hollington
*Assistant Examiner* — Temilade Rhodes-Vivour
(74) *Attorney, Agent, or Firm* — Dinsmore & Shohl LLP (57) ABSTRACT

A manufacturing method of a semiconductor device is provided with an inspecting of a semiconductor substrate by an inspection method, the method including heating the semiconductor substrate, measuring first and second characteristics. The measuring of a first characteristic is performed by bringing a plurality of probes into contact with the heated semiconductor substrate and making a first electric current flow in the semiconductor substrate. The measuring of a second characteristic is performed, after the measuring of the first characteristic, by bringing a plurality of probes into contact with the heated semiconductor substrate and making a second electric current flow in the semiconductor substrate. A number of the plurality of probes used in the measuring of the second characteristic is larger than a number of the plurality of probes used in the measuring of the first characteristic. The second electric current is larger than the first electric current.

7 Claims, 8 Drawing Sheets (51) Int. Cl.
*H01L 21/66* (2006.01)
*G01R 31/26* (2014.01)
*H01L 21/00* (2006.01)

(52) U.S. Cl.
CPC .......... *H01L 22/20* (2013.01); *G01N 2201/00* (2013.01); *H01L 21/00* (2013.01); *H01L 2221/00* (2013.01)

(56) References Cited

U.S. PATENT DOCUMENTS

| | | | |
|---|---|---|---|
| 2009/0195263 A1* | 8/2009 | Yano | G01R 31/2891 324/762.06 |
| 2010/0066393 A1* | 3/2010 | Bottoms | G01R 1/06711 324/755.05 |
| 2010/0201391 A1* | 8/2010 | Gunji | G01R 31/2875 324/750.03 |
| 2013/0053282 A1* | 2/2013 | Hashim | H01L 22/14 506/39 |
| 2013/0106453 A1 | 5/2013 | Ikegami | |
| 2014/0049283 A1* | 2/2014 | Wang | G01R 31/2635 324/762.01 |
| 2014/0086523 A1* | 3/2014 | Block | G02F 1/065 385/3 |
| 2014/0266274 A1* | 9/2014 | Shiraishi | G01R 1/07357 324/750.25 |
| 2014/0333342 A1 | 11/2014 | Akahori et al. | |
| 2015/0108002 A1* | 4/2015 | Kim | C25D 1/003 205/122 |

* cited by examiner

INSPECTION METHOD FOR SEMICONDUCTOR SUBSTRATE, MANUFACTURING METHOD OF SEMICONDUCTOR DEVICE AND INSPECTION DEVICE FOR SEMICONDUCTOR SUBSTRATE

CROSS-REFERENCE TO RELATED APPLICATION

This application claims priority to Japanese Patent Application No. 2015-038648 filed on Feb. 27, 2015, the entire contents of which are hereby incorporated by reference into the present application.

TECHNICAL FIELD

A technology disclosed in the present disclosure relates to a temperature inspection for a semiconductor substrate and a manufacturing method of a semiconductor device using the same.

DESCRIPTION OF RELATED ART

Japanese Patent Application Publication No. 2013-096837 discloses a technology to bring a large number of probes into contact with a semiconductor substrate to inspect a characteristic of the semiconductor substrate. Technologies to inspect characteristics of a semiconductor substrate in a phase prior to packaging as such have been used widely in the field of semiconductor devices. Usually, a plurality of characteristics of a semiconductor substrate is measured in one inspection.

SUMMARY

There may be a case of performing a temperature inspection in which characteristics of a semiconductor substrate are inspected while the semiconductor substrate is being heated. In the temperature inspection, a large number of probes are brought into contact with the semiconductor substrate in a heated state, and an electric current is made to flow in the semiconductor substrate. A plurality of characteristics of the semiconductor substrate can thereby be measured in a high-temperature state.

Each of the probes for being brought into contact with the semiconductor substrate has an elongated shape so as to be accurately brought into contact with electrodes of the semiconductor substrate. Accordingly, when the probes are set at a waiting position (a position where the probes are not in contact with the semiconductor substrate) prior to the inspection, they are cooled by heat exchange with the atmosphere. In a subsequent inspection, when the probes make contact with the semiconductor substrate being at a high temperature, the semiconductor substrate is cooled, causing a temporary decrease in temperature of the semiconductor substrate. It is therefore necessary to wait for the temperature of the semiconductor substrate to be stable and then measure characteristics of the semiconductor substrate. Accordingly, the conventional temperature inspection has had a problem that much time is required until the measurement of characteristics is started. The present disclosure therefore provides a technology to perform a temperature inspection in a shorter time.

One aspect of an inspection method for a semiconductor substrate disclosed in the present disclosure comprises heating the semiconductor substrate, measuring a first characteristic and measuring a second characteristic. The measuring of a first characteristic is performed by bringing a plurality of probes into contact with the heated semiconductor substrate and making a first electric current flow in the semiconductor substrate. The measuring of a second characteristic is performed, after the measuring of the first characteristic, by bringing a plurality of probes into contact with the heated semiconductor substrate and making a second electric current flow in the semiconductor substrate. A number of the plurality of probes used in the measuring of the second characteristic is larger than a number of the plurality of probes used in the measuring of the first characteristic. The second electric current is larger than the first electric current. A rate of change in the first characteristic with respect to temperature is larger than a rate of change in the second characteristic with respect to temperature.

Note that the above-described semiconductor substrate is a substrate that has a semiconductor layer. Therefore, if an electrode and an insulation layer are provided at a front surface of the semiconductor layer, the semiconductor layer, the electrode, and the insulation layer, as a whole, serve as a semiconductor substrate. Furthermore, the semiconductor substrate may be a discal semiconductor wafer, or may be a semiconductor chip formed by dividing the semiconductor wafer into chips.

Furthermore, in the present disclosure, a rate of change in a characteristic with respect to temperature means a ratio of change in a characteristic when a temperature of the semiconductor substrate changes by a unit temperature. In other words, the rate of change in a characteristic with respect to temperature means a value obtained by dividing an amount of change in the characteristic when the temperature of the semiconductor substrate changes by a unit temperature, by an absolute value of the characteristic prior to the change.

In this temperature inspection method, the first electric current that is smaller is made to flow in the semiconductor substrate to thereby measure the first characteristic, and the second electric current that is larger is made to flow in the semiconductor substrate to thereby measure the second characteristic. Since the rate of change in the first characteristic with respect to temperature is larger, it is necessary to accurately control the temperature of the semiconductor substrate in the measuring of the first characteristic. On the other hand, since the rate of change in the second characteristic with respect to temperature is smaller, it is not necessary to so accurately control the temperature of the semiconductor substrate in the measuring of the second characteristic. In this temperature inspection method, the first characteristic is measured prior to the second characteristic. In the measuring of the first characteristic, a smaller number of probes are brought into contact with the heated semiconductor substrate. Since the smaller number of probes are brought into contact with the semiconductor substrate, a decrease in temperature of the semiconductor substrate when the probes are in contact with the semiconductor substrate is smaller. Accordingly, the temperature of the semiconductor substrate becomes stable in a short time. A waiting time before starting the measurement of the first characteristic can therefore be shortened. As such, according to this method, the first characteristic can accurately be measured with a short waiting time. Furthermore, in the measuring of the second characteristic, a larger number of probes are brought into contact with the semiconductor substrate. Although the second electric current that is made to flow in the measuring of the second characteristic is larger, a larger number of probes are brought into contact with the semiconductor substrate, so that the second electric current can be made to flow in a manner the second electric current is distributed in the probes. An electric current that flows in each of the probes can thereby be reduced. Furthermore, the larger number of probes are brought into contact with the semiconductor substrate and hence a decrease in temperature of the semiconductor substrate when the probes are in contact with the semiconductor substrate is larger. The rate of change in the second characteristic with respect to temperature is however smaller, and it is therefore not necessary to so accurately control the temperature in the measuring of the second characteristic. Accordingly, it is possible to shorten a waiting time before starting the measurement of the second characteristic after bringing the probes into contact with the semiconductor substrate. Even with a short waiting time, the second characteristic can be measured with sufficient accuracy. As described above, according to this method, the first and second characteristics can be measured with sufficient accuracy. Furthermore, according to this method, the waiting time for measuring the first characteristic and the waiting time for measuring the second characteristic can be reduced. According to such a configuration, a total waiting time obtained by adding the waiting time for measuring the first characteristic and the waiting time for measuring the second characteristic can be made shorter than a waiting time in the conventional measurement method. In other words, according to this method, the first and second characteristics can be measured in a shorter time than it could have been with conventional methods.

Another aspect of an inspection method for a semiconductor substrate disclosed in the present disclosure comprises heating the semiconductor substrate, measuring a first characteristic and measuring a second characteristic. The measuring of a first characteristic is performed by bringing a plurality of probes into contact with the heated semiconductor substrate and making a first electric current flow in the semiconductor substrate. The measuring of a second characteristic is performed, after the measuring of the first characteristic, by bringing a plurality of probes into contact with the heated semiconductor substrate and making a second electric current flow in the semiconductor substrate. A number of the plurality of probes used in the measuring of the second characteristic is larger than a number of the plurality of probes used in the measuring of the first characteristic. The second electric current is larger than the first electric current. The semiconductor substrate includes a semiconductor layer and a diode which is laminated above the semiconductor layer via an insulation film. The first characteristic is a forward voltage drop of the diode.

The forward voltage drop of the diode changes in accordance with temperature. Accordingly, the diode laminated above the semiconductor layer is used as a temperature sensor for measuring a temperature of the semiconductor layer. The forward voltage drop of the diode used as a temperature sensor for measuring a temperature of the semiconductor layer requires high accuracy. Accordingly, in the temperature inspection method, it is necessary to measure the forward voltage drop of the diode with high accuracy. It is therefore necessary to accurately control the temperature of the semiconductor substrate in measuring the forward voltage drop of the diode (i.e., the first characteristic). On the other hand, the second characteristic measured with the use of the second electric current, which is large, differs from the first characteristic (the forward voltage drop of the diode), and does not require very high accuracy. Accordingly, in the measuring of the second characteristic, it is not necessary to so accurately control the temperature of the semiconductor substrate. In this inspection method, a small number of probes are brought into contact with the semiconductor substrate in the measuring of the first characteristic (the forward voltage drop of the diode), while a large number of probes are brought into contact with the semiconductor substrate in the measuring of the second characteristic. Accordingly, as in the first temperature inspection method, the first and second characteristics can be measured with sufficient accuracy in a short time.

Further, the present disclosure may provide an inspection device for a semiconductor substrate. The inspection device comprises a stage on which the semiconductor substrate is mounted, a heater heats the semiconductor substrate mounted on the stage, and a probe card including a plurality of first probes and a plurality of second probes. The probe card is located above the stage such that tips of the first and second probes face the stage. When the probe card is located above the stage, the probe card is formed such that the tips of the first probes are closer to the stage than the tips of the second probes are.

In this temperature inspection device, when the probe card is located above the stage, the tips of the first probes are closer to the stage than the tips of the second probes are. In the measuring of the first characteristic, the first probes can therefore be brought into contact with the semiconductor substrate on the stage while the second probes are not brought into contact with the semiconductor substrate on the stage. In the measuring of the second characteristic, the first and second probes can be brought into contact with the semiconductor substrate on the stage. According to this temperature inspection device, the first and second characteristics can accurately be measured in a short time.

DETAILED DESCRIPTION OF THE EMBODIMENTS

Figure 1:
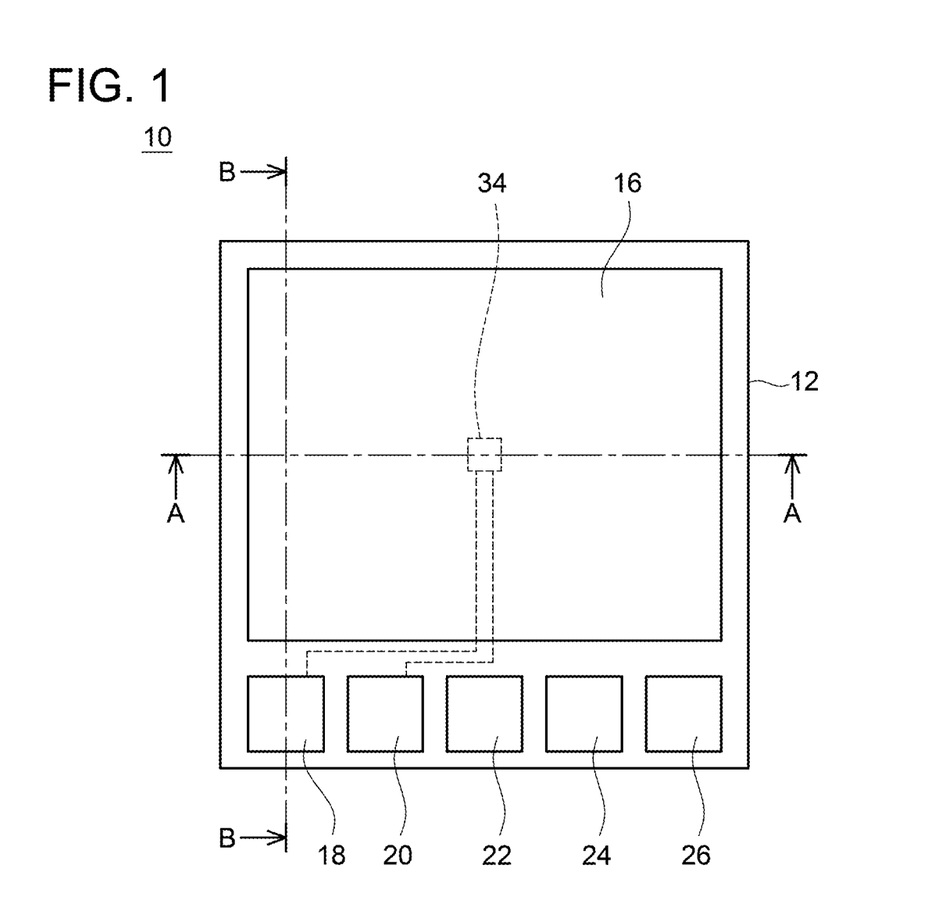
FIG. 1 shows a plan view of a semiconductor chip 10.
Figure 2:
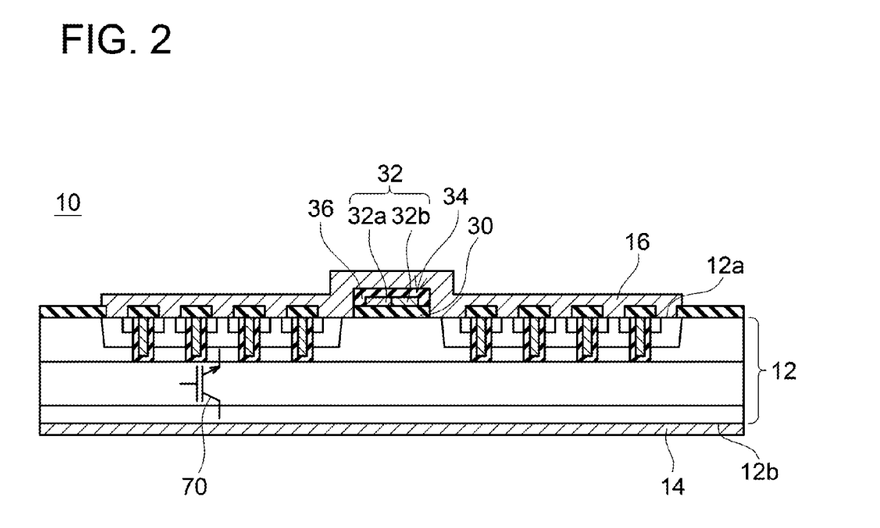
FIG. 2 shows a longitudinal cross section of the semiconductor chip 10 on a line A-A in FIG. 1.

In a temperature inspection method according to an embodiment, a semiconductor chip 10 shown in FIGS. 1 and 2 is inspected. The semiconductor chip 10 comprises a semiconductor layer 12 formed of silicon. An IGBT (Insulated Gate Bipolar Transistor) 70 is formed in the semiconductor layer 12. Furthermore, an interlayer insulation film 30 is provided at a part of a front surface 12a of the semiconductor layer 12. A polysilicon layer 32 is provided on the interlayer insulation film 30. The polysilicon layer 32 includes an anode region 32a doped with p-type impurities and a cathode region 32b doped with n-type impurities. The anode region 32a and the cathode region 32b form a diode 34. The diode 34 is insulated from the semiconductor layer 12 by the interlayer insulation film 30. A forward voltage drop in energizing the diode 34 changes depending on a temperature. In other words, the forward voltage drop of the diode 34 has a high rate of change with respect to temperature. It should be noted that the rate of change with respect to temperature means a value obtained by dividing an amount of change in a characteristic when the temperature changes by a unit temperature, by an absolute value of the characteristic prior to the change. For example, if the forward voltage drop is approximately 0.6 V at a room temperature, and an increase in temperature of the diode 34 by 50° C. causes a decrease in forward voltage drop to approximately 0.55 V, the rate of change in the forward voltage drop with respect to temperature (i.e., the rate of change in the forward voltage drop with respect to a temperature of 1° C.) is about 0.17%. The temperature of the diode 34 approximately coincides with the temperature of the semiconductor layer 12. The temperature of the semiconductor layer 12 can therefore be measured by measuring the forward voltage drop of the diode 34. In other words, the diode 34 is a temperature sense diode for detecting the temperature of the semiconductor layer 12. As such, the diode 34 is used as a sensor for detecting a temperature. Accordingly, the forward voltage drop of the diode 34 requires excessively high accuracy. A front surface of the diode 34 is covered with an interlayer insulation film 36, except for a wiring part not shown.

A collector electrode 14 for IGBT is provided at a back surface 12b of the semiconductor layer 12. An emitter electrode 16 for IGBT is provided at the front surface 12a of the semiconductor layer 12. The emitter electrode 16 is insulated from the diode 34 by the interlayer insulation film 36. As shown in FIG. 1, the emitter electrode 16 occupies most of the front surface 12a of the semiconductor layer 12. The IGBT 70 is provided in the semiconductor layer 12 below the emitter electrode 16. A plurality of electrode pads 18 to 26 are provided adjacent to the emitter electrode 16.

The anode electrode pad 18 is provided above an interlayer insulation film and insulated from the semiconductor layer 12. The anode electrode pad 18 is connected to the anode region 32a of the diode 34 by a wiring.

The cathode electrode pad 20 is provided above an interlayer insulation film and insulated from the semiconductor layer 12. The cathode electrode pad 20 is connected to the cathode region 32b of the diode 34 by a wiring.

The gate electrode pad 22 is provided above an interlayer insulation film and insulated from the semiconductor layer 12. The gate electrode pad 22 is connected to a gate electrode of the IGBT 70 by a wiring not shown.

A sense IGBT for electric current detection is provided in the semiconductor layer 12 below the electric current sense electrode pad 24. A size of the sense IGBT is smaller than a size of the IGBT 70 below the emitter electrode 16. The electric current sense electrode pad 24 is connected to an emitter of the sense IGBT. Furthermore, a collector of the sense IGBT is connected to the collector electrode 14. A gate electrode of the sense IGBT is connected to the gate electrode pad 22 by a wiring not shown.

The electrode pad 26 is a Kelvin terminal for emitter voltage measurement.

Figure 3:
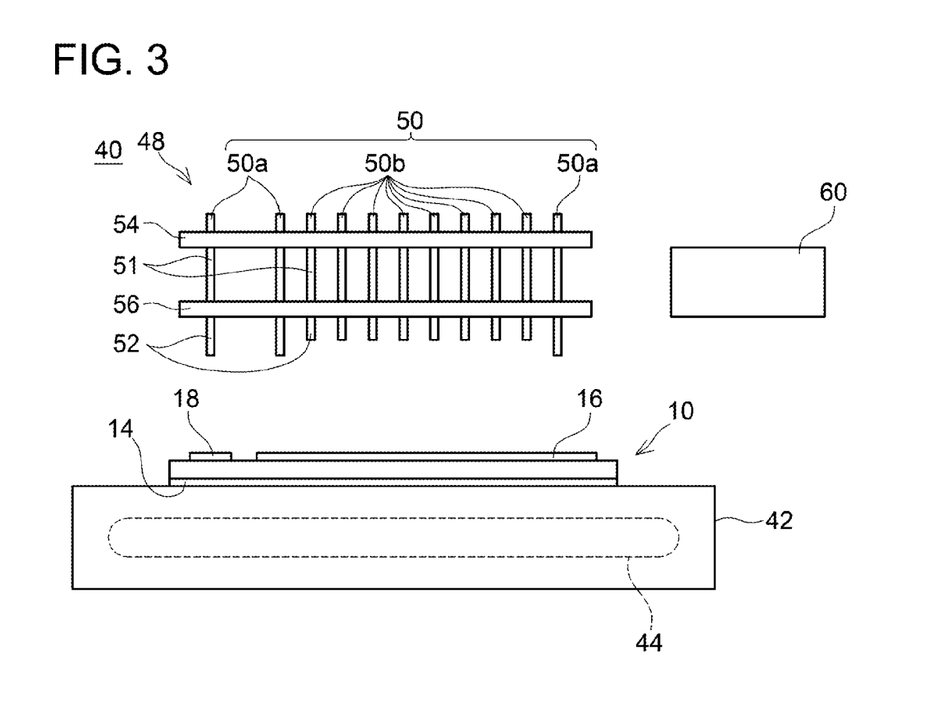
FIG. 3 shows an illustration of a temperature inspection device 40, which shows a positional relation between the semiconductor chip 10 and probes 50 on a line B-B in FIG. 1.

FIG. 3 shows a temperature inspection device 40 that performs an inspection while heating the semiconductor chip 10. The temperature inspection device 40 comprises a stage 42, a heater 44, a controller 60, and a probe card 48. The semiconductor chip 10 to be inspected is mounted on the stage 42. The stage 42 is formed as a conductor, and also serves as an electrode. With the stage 42, a potential of the collector electrode 14 at the back surface of the semiconductor chip 10 can be controlled. The heater 44 is installed inside the stage 42. The heater 44 heats the semiconductor chip 10 mounted on the stage 42. The stage 42 is moving with the heater 44 in a lateral direction. As shown in FIG. 3, the stage 42 can move between a position immediately below the probe card 48 (an inspection position) and a waiting position (a position apart from the inspection position) not shown.

Figure 7:
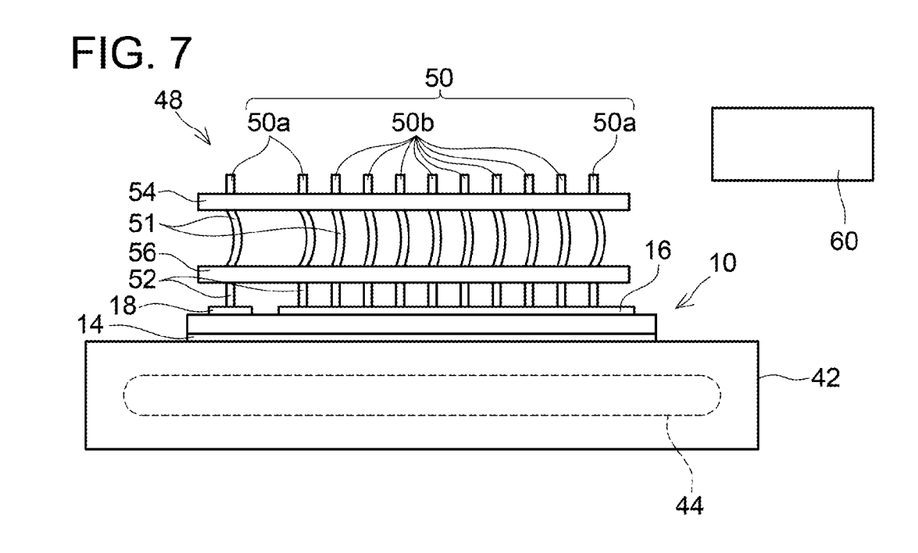
FIG. 7 shows an illustration that corresponds to FIG. 3, which shows a state where the first probes 50a and second probes 50b are in contact with the semiconductor chip 10.

The probe card 48 is a so-called vertical-type probe card, and has a large number of probes 50 that extend in upward and downward directions (i.e., an approximately vertical direction relative to the stage 42). The probe card 48 includes a fixing plate 54 and a guide plate 56. The probes 50 are fixed to the fixing plate 54. The guide plate 56 is located under the fixing plate 54. A spacing is provided between the guide plate 56 and the fixing plate 54. The guide plate 56 has a large number of guide holes, and each of the guide holes has a probe 50 inserted therethrough, respectively. The probes 50 are not fixed to the guide plate 56, and can slide relative to the guide plate 56. Note that the probes 50 include first probes 50a each having a protruding part 52 with a long length and second probes 50b each having a protruding part 52 with a short length, the protruding parts 52 protruding from the guide plate 56 in a downward direction. Each of the probes 50 has a flexible part 51 between the fixing plate 54 and the guide plate 56. The probe card 48 can advance toward and retract from the stage 42. By moving the probe card 48 from a position shown in FIG. 3 toward the stage 42, the probes 50 can be brought into contact with the semiconductor chip 10 as shown in FIG. 7, for example. As shown in FIG. 7, when tips of the probes 50 make contact with the semiconductor chip 10, the flexible parts 51 are warped.

The controller 60 controls movements of the stage 42 and the probe card 48. Furthermore, the controller 60 is connected to each of the probes 50 by a wiring not shown. The controller 60 controls each part of the temperature inspection device 40 and performs a temperature inspection.

Next, a temperature inspection method with the use of the temperature inspection device 40 will be described. The temperature inspection device 40 is used in a step of manufacturing a semiconductor device. In other words, in the step of manufacturing the semiconductor device, a prescribed processing is performed on a semiconductor wafer, and the semiconductor wafer is diced to thereby manufacture the semiconductor chips 10. Thereafter, a temperature inspection step is performed on each semiconductor chip 10. The semiconductor chip 10 that has passed the temperature inspection step is mounted on a lead frame and sealed with resin. A semiconductor device is thereby completed. In other words, a semiconductor device is manufactured through the temperature inspection step. The temperature inspection device 40 is used in the temperature inspection step for the semiconductor chip 10. The temperature inspection step for the semiconductor chip 10 is performed by the controller 60 of the temperature inspection device 40 performing processes shown in FIG. 4.

Figure 4:
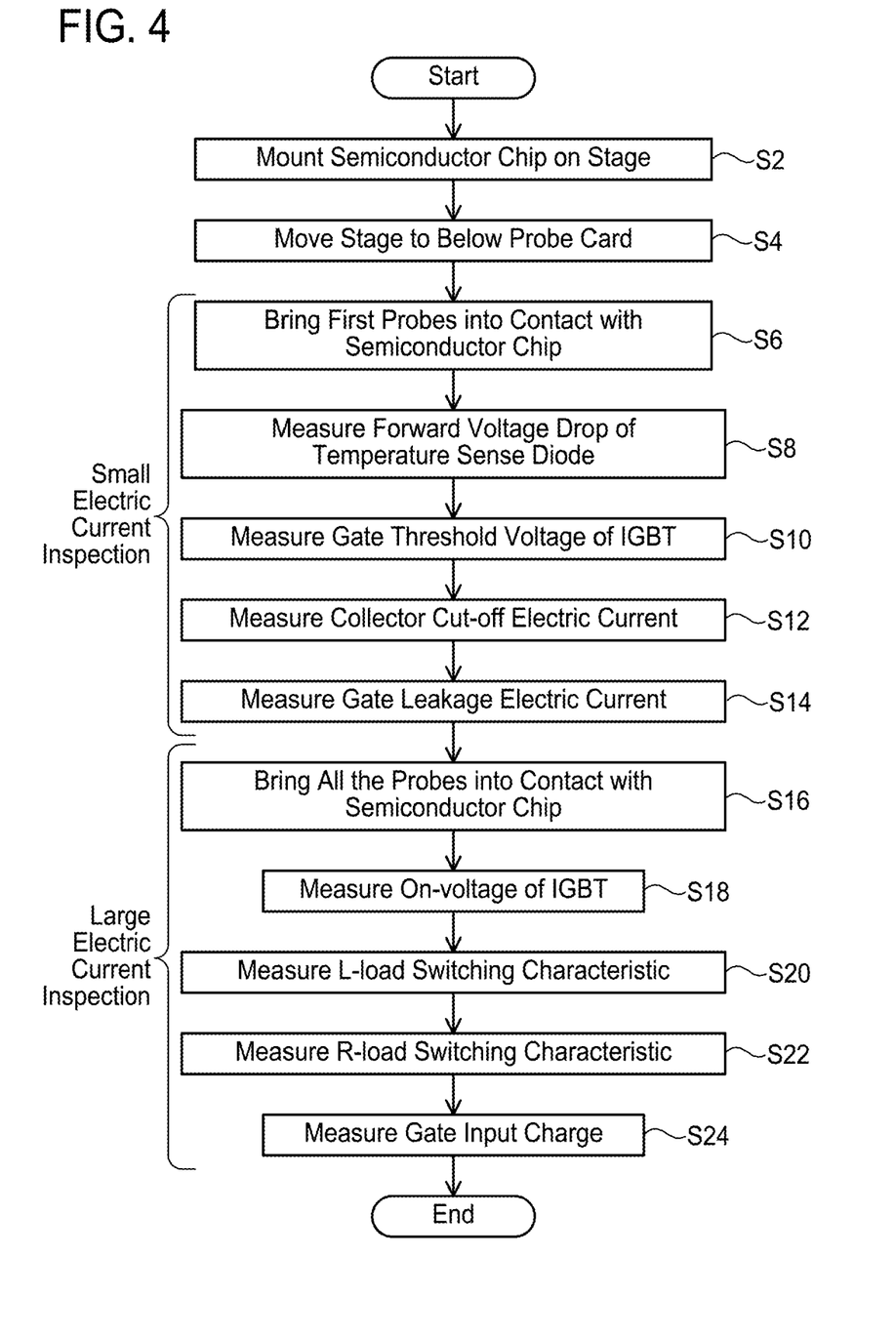
FIG. 4 shows a flowchart that shows a temperature inspection method.

Note that the temperature inspection shown in FIG. 4 is repeatedly performed by the temperature inspection device 40. When the probes 50 of the probe card 48 are brought into contact with a semiconductor chip in a previous temperature inspection, the probes 50 are heated by the semiconductor chip. However, when the previous temperature inspection has terminated and the probes 50 have separated from the semiconductor chip, the probes 50 are cooled by atmosphere. At an interval until the start of the next temperature inspection, the temperature of the probes 50 is decreased by approximately 10° C.

At the start of the processes in FIG. 4, the stage 42 is located at the waiting position (i.e., the position not immediately below the probe card 48). Furthermore, the heater 44 has already been operated, and the stage 42 is heated. In step S2, the semiconductor chip 10 is mounted on the stage 42 by a carrying device not shown. The semiconductor chip 10 thereby starts to be heated. Next in step S4, the controller 60 causes the stage 42 to move from the waiting position to the inspection position (i.e., the position immediately below the probe card 48, as shown in FIG. 3). While the stage 42 is being moved, the semiconductor chip 10 is heated by the heater 44. In a phase where the stage 42 has reached the inspection position, the temperature of the semiconductor chip 10 is stable at about 150° C.

Next, the controller 60 performs a small electric current inspection in steps S6 to S14. In the small electric current inspection, the controller 60 makes a relatively small electric current flow in the semiconductor chip 10 to measure various characteristics.

Figure 5:
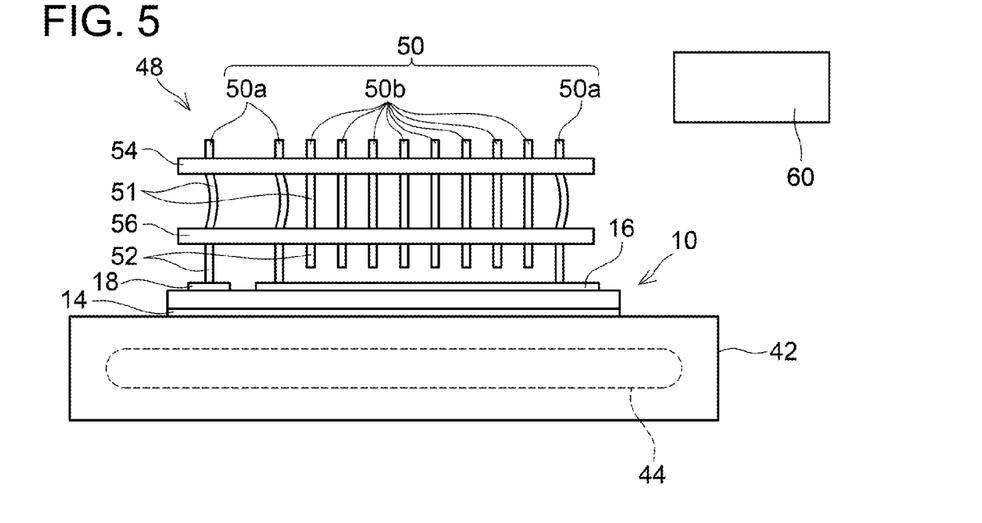
FIG. 5 shows an illustration that corresponds to FIG. 3, which shows a state where first probes 50a are in contact with the semiconductor chip 10.
Figure 6:
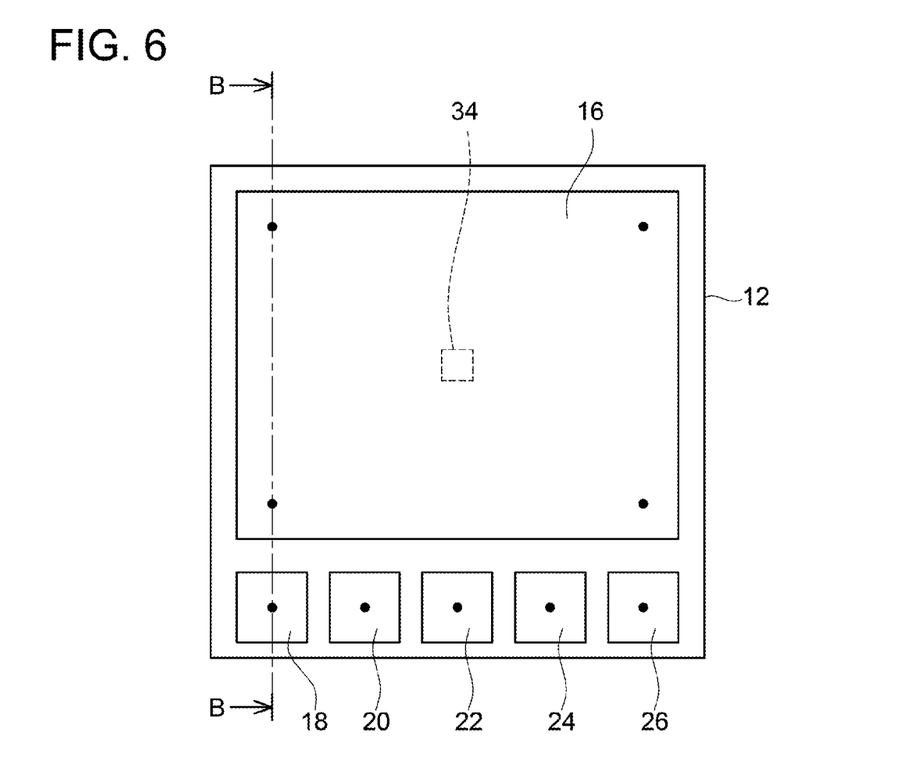
FIG. 6 shows a plan view that corresponds to FIG. 1, which shows contact points of the first probes 50a by dots.

In step S6, the controller 60 causes the probe card 48 to move toward the stage 42. As shown in FIG. 5, the controller 60 then causes the probe card 48 to stop at a position where the first probes 50*a*, which have a large protruding amount, make contact with the semiconductor chip 10 and the second probes 50*b*, which have a small protruding amount, do not make contact with the semiconductor chip 10. At this occasion, as shown by dots in FIG. 6, each of the five first probes 50*a* is brought into contact with a corresponding one among the electrode pads 18 to 26. Furthermore, four first probes 50*a* are brought into contact with the emitter electrode 16.

As described above, the probes 50 are cooled by heat exchange with the atmosphere during an interval of the temperature inspections, and thus the probes 50 are at a temperature lower than that of the semiconductor chip 10. Accordingly, when the first probes 50*a* are brought into contact with the semiconductor chip 10 being at a high temperature, the semiconductor chip 10 is cooled by the first probes 50*a*. In step S6, however, a number of first probes 50*a* that are brought into contact with the semiconductor chip 10 is small, and hence an amount of decrease in temperature of the semiconductor chip 10 is extremely small. Accordingly, after the decrease in temperature, the heating by the heater 44 causes the temperature of the semiconductor chip 10 to return to the original temperature (about 150° C.) in a short time. In the present embodiment, the controller 60 waits for about five seconds after the first probes 50*a* make contact with the semiconductor chip 10. During this waiting time (i.e., in equal to or less than five seconds after the contact of the first probes 50*a* with the semiconductor chip 10), the temperature of the semiconductor chip 10 returns to the temperature approximately equal to the original temperature.

In step S8, the controller 60 applies, between the anode electrode pad 18 and the cathode electrode pad 20, a voltage that causes the anode electrode pad 18 to have a higher potential. A constant reference electric current is thereby made to flow in the diode 34. The controller 60 measures a potential difference between the anode electrode pad 18 and the cathode electrode pad 20 when the above-described reference electric current flows (i.e., a forward voltage drop of the diode 34). As described above, the forward voltage drop of the diode 34 is used for temperature detection. Accordingly, the forward voltage drop requires extremely high accuracy. In measuring the forward voltage drop, it is therefore necessary to accurately control the temperature of the semiconductor chip 10. Furthermore, the forward voltage drop easily changes depending on the temperature. In other words, the forward voltage drop has a large rate of change with respect to temperature. In this regard as well, in measuring the forward voltage drop, it is necessary to accurately manage the temperature of the semiconductor chip 10. As described above, at the start of step S8, the temperature of the semiconductor chip 10 is stable at about 150° C. Therefore in step S8, the forward voltage drop of the diode 34 that has been heated to about 150° C. can accurately be measured.

Next, in step S10, the controller 60 measures a gate threshold voltage of an IGBT. In other words, the controller 60 gradually increases a voltage of the gate electrode pad 22 (i.e., a gate voltage of the IGBT) while measuring a collector electric current of the IGBT, in a state where a constant forward voltage is applied between the collector electrode 14 and the emitter electrode 16. The controller 60 then measures the gate voltage when the collector electric current reaches a reference value, as a gate threshold voltage. Since the temperature of the semiconductor chip 10 is stable at about 150° C. in the measurement of the gate threshold voltage, and hence the gate threshold voltage when the semiconductor chip 10 is heated to about 150° C. can accurately be measured.

Next, in step S12, the controller 60 measures a collector cut-off electric current. Here, the controller 60 applies a prescribed high potential to the collector electrode 14, in a state where a same potential is applied to the emitter electrode 16 and the gate electrode pad 22 (i.e., a state where the IGBT is off). The controller 60 thereby measures a leakage electric current that flows in the IGBT (i.e., the collector cut-off electric current). Since the temperature of the semiconductor chip 10 is stable at about 150° C. in measuring the collector cut-off electric current, the collector cut-off electric current when the semiconductor chip 10 is heated to about 150° C. can accurately be measured.

Next, in step S14, the controller 60 measures a gate leakage electric current. Here, the controller 60 applies a prescribed high potential to the gate electrode pad 22, in a state where a same potential is applied to the collector electrode 14 and the emitter electrode 16. The controller 60 thereby measures a leakage electric current that flows in the IGBT (i.e., a gate leakage electric current). Since the temperature of the semiconductor chip 10 is stable at about 150° C. in the measurement of gate leakage electric current, the gate leakage electric current when the semiconductor chip is heated to about 150° C. can accurately be measured.

When the small electric current inspection in steps S6 to S14 has completed, the controller 60 then performs a large electric current inspection in steps S16 to S24. In the large electric current inspection, a relatively large electric current is made to flow in the semiconductor chip 10 to thereby inspect various characteristics of the semiconductor chip 10.

Figure 8:
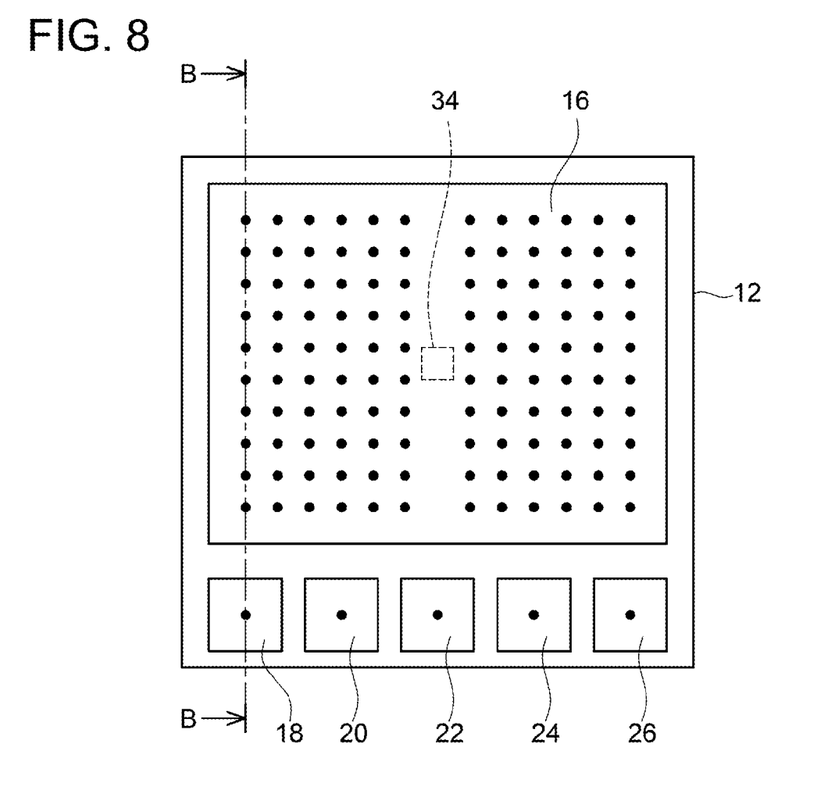
FIG. 8 shows a plan view that corresponds to FIG. 1, which shows contact points of the first and second probes 50a and 50b by dots.

In step S16, the controller 60 causes the probe card 48 to move from a position in FIG. 5 further toward the stage 42. As shown in FIG. 7, the second probes 50b, which have the small protruding amount, are then brought into contact with the semiconductor chip 10. In other words, all of the first probes 50a and the second probes 50b are brought into contact with the semiconductor chip 10. As shown by dots in FIG. 8, a large number of probes 50 thereby make contact with the emitter electrode 16. The temperature of the second probes 50b in the state of not being in contact with the semiconductor chip 10 is lower than the temperature of the semiconductor chip 10. In step S16, when the second probes 50b have been brought into contact with the semiconductor chip 10, the temperature of the semiconductor chip 10 is decreased. In step S16, since the large number of second probes 50b are brought into contact with the semiconductor chip 10, the temperature of the semiconductor chip 10 is significantly decreased. With a subsequent waiting, the heating by the heater 44 causes the temperature of the semiconductor chip 10 to return to the original temperature (150° C.), which however requires a long time (e.g., about 30 seconds). The controller 60, without waiting for the temperature of the semiconductor chip 10 to return to the original temperature, performs step S18. In other words, the controller 60 performs step S18 immediately upon bringing the second probes 50b into contact with the semiconductor chip 10.

In step S18, the controller 60 measures an ON-voltage of the IGBT. In other words, a prescribed load is connected to the IGBT, and a constant forward voltage is applied to a series circuit made of the IGBT and the load. A constant voltage higher than the gate threshold voltage is then applied to the gate electrode pad 22 to turn on the IGBT. A collector electric current is thereby made to flow in the IGBT to measure a voltage (i.e., an ON-voltage) between the collector electrode 14 and the emitter electrode 16 at this occasion. As described above, the controller 60 performs the ON-voltage measurement immediately upon bringing the second probes 50b into contact with the semiconductor chip 10. The temperature of the semiconductor chip 10 in the measuring of the ON-voltage is therefore not so accurately managed. However, the ON-voltage does not require very high accuracy. In other words, an acceptable range allowed with respect to an ON-voltage is wider than an acceptable range allowed with respect to a forward voltage drop of the diode 34. It is therefore not necessary to so accurately manage the temperature of the semiconductor chip 10 in the measuring of an ON-voltage. In other words, the ON-voltage can be measured with sufficient accuracy even if the temperature of the semiconductor chip 10 in the measuring of an ON-voltage is not so accurately managed. Furthermore, in step S18, since a large number of probes 50 are brought into contact with the emitter electrode 16, an electric current flows such that the current is distributed among the plurality of probes. Accordingly, even if a large collector electric current flows in the IGBT 70, no significant problem occurs.

Figure 9:
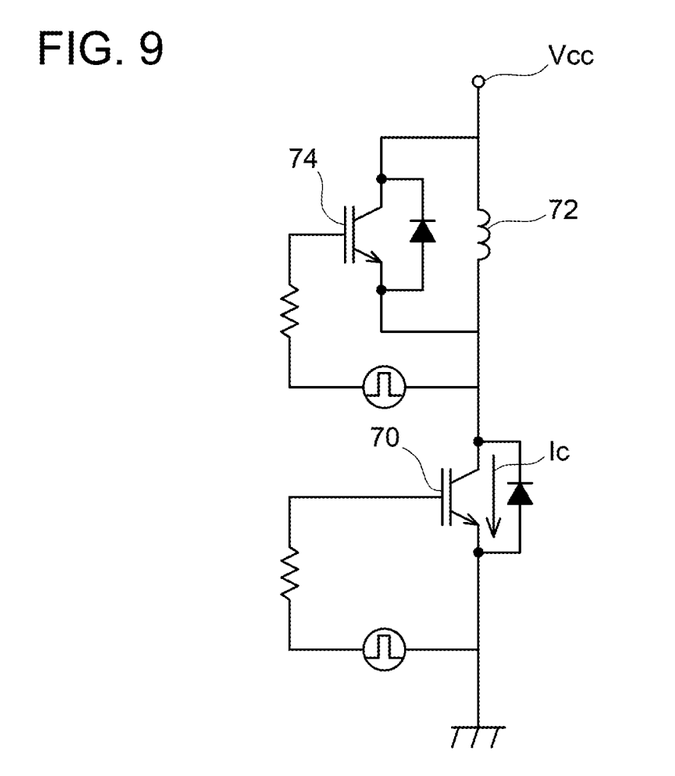
FIG. 9 shows a circuit diagram of a measuring circuit for an L-load switching characteristic.
Figure 10:
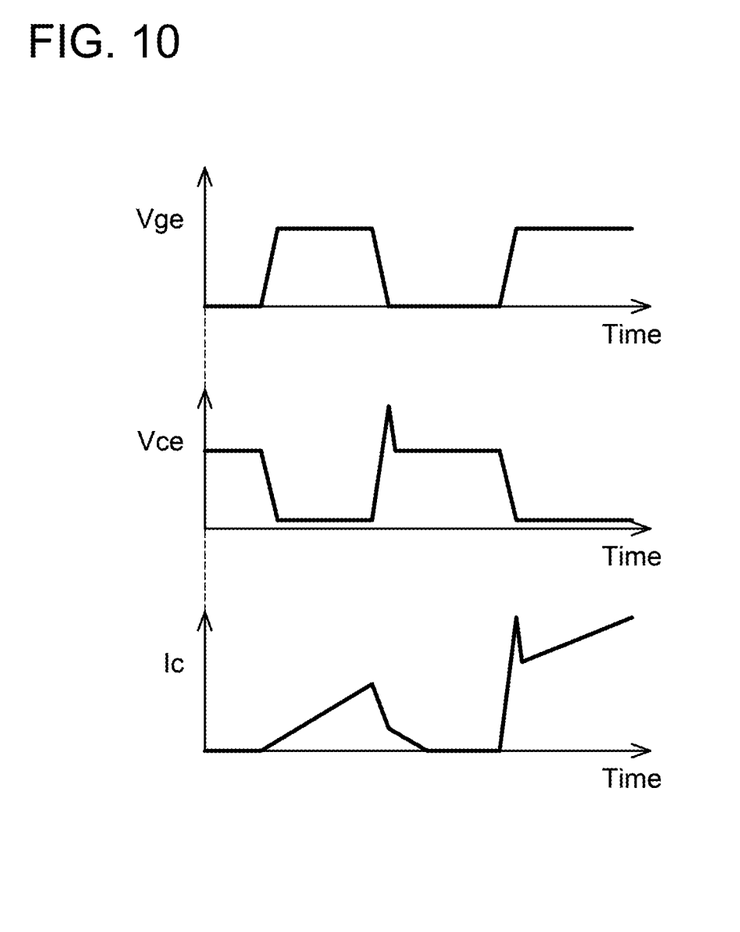
FIG. 10 shows a graph that shows waveforms of a gate voltage Vge, a collector-emitter voltage Vce, and a collector electric current Ic in measuring the L-load switching characteristic.

Next, in step S20, the controller 60 measures an L-load switching characteristic of the IGBT. The L-load switching characteristic is measured by a circuit shown in FIG. 9. One end of a coil 72 is connected to the collector of the IGBT 70, while the other end of the coil 72 is connected to a high potential Vcc. The emitter of the IGBT 70 is connected to a ground potential. Furthermore, another IGBT 74 is connected to the coil 72 in parallel. Diodes are connected to the IGBTs 70 and 74, respectively, in anti-parallel. Under a state where the circuit is formed as such, a pulse-like voltage is repeatedly applied alternately to the gate of the IGBT 70 and the gate of the IGBT 74. In other words, the IGBT 70 and the IGBT 74 are alternately turned on. Consequently, as shown in FIG. 10, a gate voltage Vge, a collector-emitter voltage Vce, and a collector electric current Ic of the IGBT 70 change. The controller 60 measures a turn-on speed and a turn-off speed (i.e., the L-load switching characteristic) of the IGBT 70 based on waveforms of the collector-emitter voltage Vce and the collector electric current Ic. Since the measurement of the L-load switching characteristic is performed immediately after the measurement of the ON-voltage in step S18, the temperature of the semiconductor chip 10 in measuring the L-load switching characteristic is not so accurately managed. However, the L-load switching characteristic does not require very high accuracy. It is therefore not necessary to so accurately manage the temperature of the semiconductor chip 10 in the measurement of an L-load switching characteristic. In other words, the L-load switching characteristic can be measured with sufficient accuracy even if the temperature of the semiconductor chip 10 in the measurement of an L-load switching characteristic is not so accurately managed. Furthermore, the L-load switching characteristic has a small rate of change with respect to temperature. In this regard as well, it is not necessary to so accurately manage the temperature of the semiconductor chip 10 in measuring the L-load switching characteristic. In other words, the L-load switching characteristic can be measured with sufficient accuracy even if the temperature in measuring that characteristic is not so accurately managed. Furthermore, in step S20, since the large number of probes 50 are brought into contact with the emitter electrode 16, no significant problem occurs even if a large collector electric current flows in the IGBT 70.

Next, in step S22, an R-load switching characteristic is measured. Furthermore, in step S24, a gate input charge is measured. These characteristics are measured by making a relatively large electric current flow in the semiconductor chip 10. In steps S22 and S24, since the large number of probes 50 are brought into contact with the emitter electrode 16, no significant problem occurs even if a large electric current flows in the semiconductor chip 10. Furthermore, the R-load switching characteristic and the gate input charge do not require very high accuracy, and furthermore, each of them has a small rate of change with respect to temperature. These characteristics can therefore be measured with sufficient accuracy even if the temperature is not so accurately managed in the measuring of these characteristics.

When step S24 terminates, the temperature inspection is completed. The controller 60 transports the semiconductor chip 10 to a next step if all of the measured inspection items fall within the acceptable range. Furthermore, the controller 60 removes a semiconductor chip 10 from a manufacturing line if any of the inspection items fails to fall within the acceptable range for the semiconductor chip 10. The controller 60 repeatedly performs the process shown in FIG. 4 to thereby inspect a large number of semiconductor chips 10. As described above, in the small electric current inspection, a smaller number of probes 50 are brought into contact with the semiconductor chip 10 than that in the large electric current inspection, to thereby suppress a decrease in temperature of the semiconductor chip 10. Accordingly, in a short time after the probes 50 are brought into contact with the semiconductor chip 10, the temperature of the semiconductor chip 10 becomes stable. Accordingly, the forward voltage drop of the diode 34 can accurately be measured even if the waiting time after bringing the probes 50 into contact with the semiconductor chip 10 is shortened. Furthermore, the short waiting time aims for a reduction in time required for the small electric current inspection. Furthermore, in the large electric current inspection, the large number of probes 50 are brought into contact with the semiconductor chip 10, and then the measurements of the ON-voltage, the L-load switching characteristic, the R-load switching characteristic, and the gate input charge are started without waiting for the temperature of the semiconductor chip 10 to become stable. These characteristics do not require very high accuracy. Furthermore, the rate of change in each of the L-load switching characteristic, the R-load switching characteristic, and the gate input charge with respect to temperature is not so high. Accordingly, these characteristics can be measured with sufficient accuracy even if the waiting time is shortened (i.e., even if the temperature in the measuring of these characteristics is not so accurately controlled). Furthermore, the short waiting time aims for a reduction in time required for the large electric current inspection. According to this temperature inspection method, the semiconductor chip 10 can therefore be inspected in a short time.

Furthermore, in the above-described embodiment, the gate threshold voltage, the collector cut-off electric current, and the gate leakage electric current of the IGBT are measured with the small number of the first probes 50a. However, accuracy required for these characteristics is not so high as that required for the forward voltage drop of the diode 34. Furthermore, the rates of change in these characteristics with respect to temperature are not so large as that of the forward voltage drop of the diode 34. These characteristics may therefore be measured with a large number of the first probes 50a and the second probes 50b as in the large electric current inspection.

Furthermore, in the above-described large electric current inspection, although the on-voltage, the L-load switching characteristic, the R-load switching characteristic, and the gate input charge are measured, all of these do not necessarily have to be measured. One or a plurality of these characteristics may be measured. Furthermore, another characteristic exhibited when a large electric current flows may be measured in the large electric current inspection.

Furthermore, in the above-described embodiment, the forward voltage drop of the diode 34 is measured in the small electric current inspection. However, characteristics that are other than the forward voltage drop of the diode 34 and have a higher rate of change with respect to temperature than that of any characteristic measured in the large electric current inspection, may be measured in the small electric current inspection.

Furthermore, in the above-described embodiment, the semiconductor chip 10 is inspected. However, the semiconductor wafer obtained before being divided into the semiconductor chips 10 may be inspected by the above-described method.

Relations between each component in the above-described embodiment and each component in the claims will hereinafter be described. The forward voltage drop of the diode 34 in the embodiment is an example of the first characteristic in the claims. The L-load switching characteristic, the R-load switching characteristic, and the gate input charge in the embodiment are an example of the second characteristic in the claims that satisfies a relation in which the rate of change in the first characteristic with respect to temperature is larger than the rate of change in the second characteristic with respect to temperature. The on-voltage, the L-load switching characteristic, the R-load switching characteristic, and the gate input charge in the embodiment are an example of the second characteristic in the claims that is measured after the forward voltage drop of the diode (i.e., the characteristic that does not require very high accuracy). The fixing plate 54 and the guide plate 56 in the embodiment are an example of the support body in the claims.

Some advantages of the technique disclosed in the present disclosure are summarized below. In one aspect of an inspection method disclosed in the present disclosure, a probe card may be used to perform the inspection method. The probe card comprises a support body, a plurality of first probes protruding from the support body, and a plurality of second probes protruding from the support body. The first probes protrude from the support body longer than the second probes. In the measuring of the first characteristic, the first probes are brought into contact with the semiconductor substrate and the second probes are not brought into contact with the semiconductor substrate. In the measuring of the second characteristic, the first and second probes are brought into contact with the semiconductor substrate.

According to the above the inspection method, the first characteristic and the second characteristic can be easily measured.

While specific examples of the present disclosure have been described above in detail, these examples are merely illustrative and place no limitation on the scope of the claims. The technology described in the claims also encompasses various changes and modifications to the specific examples described above. The technical elements explained in the present description or drawings provide technical utility either independently or through various combinations. The present disclosure is not limited to the combinations described at the time the claims are filed. Further, the purpose of the examples illustrated by the present description or drawings is to satisfy multiple objectives simultaneously, and satisfying any one of those objectives gives technical utility to the present disclosure.

What is claimed is:

1. An inspection method for a semiconductor substrate, the method comprising:
   heating the semiconductor substrate;
   measuring a first characteristic by bringing a plurality of probes into contact with the heated semiconductor substrate and making a first electric current flow in the semiconductor substrate; and
   measuring a second characteristic, after the measuring of the first characteristic, by bringing a plurality of probes into contact with the heated semiconductor substrate and making a second electric current flow in the semiconductor substrate, wherein a number of the plurality of probes used in the measuring of the second characteristic is larger than a number of the plurality of probes used in the measuring of the first characteristic, and the second electric current is larger than the first electric current,
   wherein a rate of change in the first characteristic with respect to temperature is larger than a rate of change in the second characteristic with respect to temperature.

2. The inspection method according to claim 1, wherein a probe card is used to perform the inspection method,
   the probe card comprises a support body, a plurality of first probes protruding from the support body, and a plurality of second probes protruding from the support body,
   the first probes protrude from the support body longer than the second probes,
   in the measuring of the first characteristic, the first probes are brought into contact with the semiconductor substrate and the second probes are not brought into contact with the semiconductor substrate, and in the measuring of the second characteristic, the first and second probes are brought into contact with the semiconductor substrate.

3. A manufacturing method of a semiconductor device, the method comprising:

inspecting a semiconductor substrate by performing the inspection method for the semiconductor substrate according to claim 1.

4. An inspection method for a semiconductor substrate, the method comprising:

heating the semiconductor substrate;

measuring a first characteristic by bringing a plurality of probes into contact with the heated semiconductor substrate and making a first electric current flow in the semiconductor substrate; and measuring a second characteristic, after the measuring of the first characteristic, by bringing a plurality of probes into contact with the heated semiconductor substrate and making a second electric current flow in the semiconductor substrate, wherein a number of the plurality of probes used in the measuring of the second characteristic is larger than a number of the plurality of probes used in the measuring of the first characteristic, and the second electric current is larger than the first electric current, wherein the semiconductor substrate includes a semiconductor layer and a diode which is laminated above the semiconductor layer via an insulation film, and the first characteristic is a forward voltage drop of the diode.

5. The inspection method according to claim 4, wherein a probe card is used to perform the inspection method, the probe card comprises a support body, a plurality of first probes protruding from the support body, and a plurality of second probes protruding from the support body, the first probes protrude from the support body longer than the second probes, in the measuring of the first characteristic, the first probes are brought into contact with the semiconductor substrate, and the second probes are not brought into contact with the semiconductor substrate, and in the measuring of the second characteristic, the first and second probes are brought into contact with the semiconductor substrate.

6. A manufacturing method of a semiconductor device, the method comprising:

inspecting a semiconductor substrate by performing the inspection method for the semiconductor substrate according to claim 4.

7. An inspection device for a semiconductor substrate, the device comprising:

a stage on which the semiconductor substrate is mounted;

a heater that heats the semiconductor substrate mounted on the stage;

a probe card including a plurality of first probes and a plurality of second probes, wherein the probe card is located above the stage such that tips of the first and second probes face the stage, and when the probe card is located above the stage the tips of the first probes are closer to the stage than the tips of the second probes; and a controller configured to perform measurement of a first characteristic and measurement of a second characteristic in this order, wherein the controller is configured to perform:

measuring the first characteristic by bringing the first probes into contact with the semiconductor substrate on the stage while not bringing the second probes into contact with the semiconductor substrate on the stage and by making a first electric current flow in the semiconductor substrate; and measuring the second characteristic by bringing the first and second probes into contact with the semiconductor substrate on the stage and by making a second electric current flow in the semiconductor substrate, wherein the second electric current is larger than the first electric current.

* * * * *

UNITED STATES PATENT AND TRADEMARK OFFICE
CERTIFICATE OF CORRECTION

PATENT NO. : 9,753,082 B2
APPLICATION NO. : 15/055200
DATED : September 5, 2017
INVENTOR(S) : Yohei Iwahashi and Hidemi Senda It is certified that error appears in the above-identified patent and that said Letters Patent is hereby corrected as shown below:

In Column 14, Line 19, Claim 7, after "second probes," delete "wherein".

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*